(12) United States Patent
Daugharthy et al.

(10) Patent No.: US 11,697,839 B2
(45) Date of Patent: *Jul. 11, 2023

(54) METHODS FOR DETECTING AND IDENTIFYING GENOMIC NUCLEIC ACIDS

(71) Applicant: President and Fellows of Harvard College, Cambridge, MA (US)

(72) Inventors: Evan R. Daugharthy, Cambridge, MA (US); Son C. Nguyen, West Roxbury, MA (US); Chao-ting Wu, Brookline, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 269 days.

This patent is subject to a terminal disclaimer.

(21) Appl. No.: 17/068,893

(22) Filed: Oct. 13, 2020

(65) Prior Publication Data

US 2021/0040548 A1 Feb. 11, 2021

Related U.S. Application Data

(63) Continuation of application No. 16/085,705, filed as application No. PCT/US2017/022942 on Mar. 17, 2017, now Pat. No. 10,844,426.

(60) Provisional application No. 62/309,714, filed on Mar. 17, 2016.

(51) Int. Cl.
*C12Q 1/6841* (2018.01)
*C40B 70/00* (2006.01)
*C40B 40/08* (2006.01)
*C12Q 1/6816* (2018.01)
*C40B 20/04* (2006.01)

(52) U.S. Cl.
CPC ......... *C12Q 1/6841* (2013.01); *C12Q 1/6816* (2013.01); *C40B 40/08* (2013.01); *C40B 70/00* (2013.01); *C40B 20/04* (2013.01)

(58) Field of Classification Search
None
See application file for complete search history.

(56) References Cited

U.S. PATENT DOCUMENTS

| 2008/0269068 | A1 | 10/2008 | Church et al. |
| 2010/0304994 | A1 | 12/2010 | Wu et al. |
| 2011/0092387 | A1 | 4/2011 | Monforte |
| 2012/0065091 | A1 | 3/2012 | Willis et al. |

OTHER PUBLICATIONS

Metzker et al. "Sequencing technologies—the next generation," Nature Reviews Genetics, Dec. 8, 2009 (Dec. 8, 2009), vol. 11, No. 1, pp. 31-46. entire document.

Metfies et al. "An optimized protocol for the identification of diatoms, flagellated algae and pathogenic protozoa with phylochips," Molecular Ecology Notes, Jul. 19, 2007 (Jul. 19, 2007), vol. 7, pp. 925-936. entire document.

*Primary Examiner* — Kaijiang Zhang
(74) *Attorney, Agent, or Firm* — Banner & Witcoff, Ltd.

(57) ABSTRACT

The present invention relates to a method of identifying a target genomic nucleic acid sequence including hybridizing a set of probes to the target genomic nucleic acid sequence, wherein the set of probes has a unique associated barcode sequence for identification of the target genomic nucleic acid sequence, wherein each probe of the set includes (1) a complementary sequence complementary to a first strand of the target genomic nucleic acid sequence and (2) the associated barcode sequence or a portion of the associated barcode sequence, sequencing the associated barcode sequence from probes hybridized to the target genomic nucleic acid sequence using a fluorescence-based sequencing method, and identifying the target genomic nucleic acid sequence by the sequenced barcode sequence.

20 Claims, 5 Drawing Sheets
(2 of 5 Drawing Sheet(s) Filed in Color)

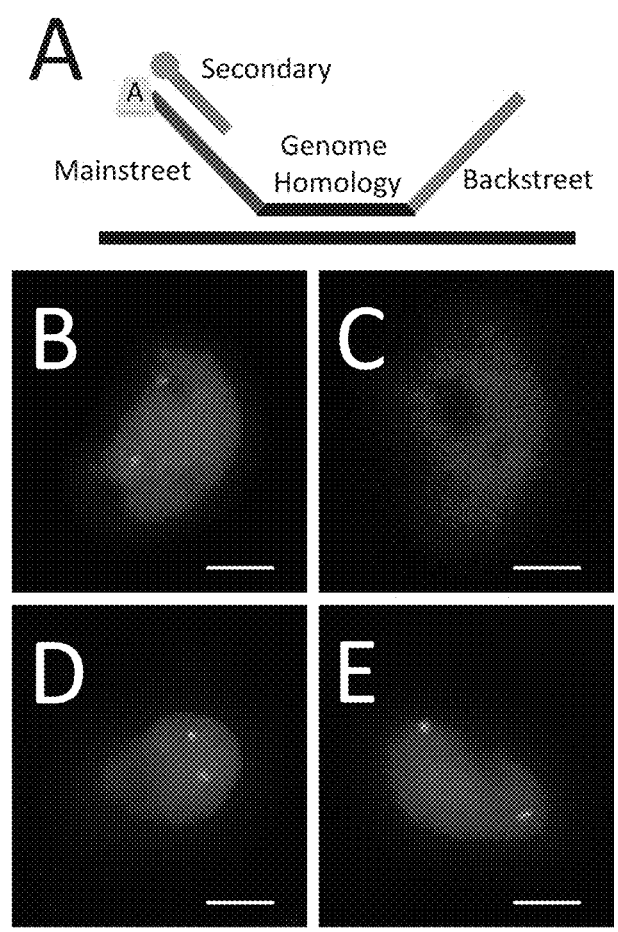
Figure 6 A-E

METHODS FOR DETECTING AND IDENTIFYING GENOMIC NUCLEIC ACIDS

RELATED APPLICATIONS

This application is a continuation application which claims priority to U.S. patent application Ser. No. 16/085,705, filed on Sep. 17, 2018, which application is a National Stage Application under 35 U.S.C. 371 of PCT application PCT/US17/22942 designating the United States and filed Mar. 17, 2017; which claims the benefit of U.S. provisional application No. 62/309,714 and filed Mar. 17, 2016 each of which are hereby incorporated by reference in their entireties.

STATEMENT OF GOVERNMENT INTERESTS

This invention was made with government support under HG005550 and GM085169 and GM106412 awarded by National Institutes of Health (NIH). The government has certain rights in this invention.

FIELD

The present invention relates in general to methods of in situ sequencing of barcodes associate with oligonucleotide probes hybridized to a target genomic nucleic acid. In this manner, methods and compositions for detecting, sequencing, identifying, measuring, counting, and/or segmenting genomic features in cells are provided.

BACKGROUND

Nucleic acids may be imaged in situ using nucleic acid hybridization methods. For genomic imaging in situ, short or long probes modified with fluorophores or other detecting moieties are hybridized to the genome. For example, short oligonucleotide probes are hybridized to the genome, where each probe bears either one or more fluorescent moieties, or one or more sites for secondary hybridization by a fluorophore-bearing oligonucleotide. However, the multiplexity of this method, e.g. the number of distinct genomic loci able to be labeled, is limited to either F×N using F spectrally distinct fluorescent moieties to label F genomic loci in each of N cycles of probe hybridization, or is bounded by N×k using k combinations of fluorescent signals, each comprised of a specific number and/or combination of the F spectrally distinct fluorophores, referred to as "colorimetric" barcoding (e.g. red+blue as a distinct label, or 2× red vs 1× red if various levels of red can be distinguished). Unfortunately this number is far fewer than the number of genomic loci, which meaningfully extends into the millions. Accordingly, methods of multiplexing the detection of a large number of genomic loci is needed.

SUMMARY

The present disclosure provides probes including one or more barcodes that can be used to hybridize to target genomic nucleic acids. The barcodes may be sequenced using a fluorescence-based sequencing method to detect and identify the target genomic nucleic acids.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawing in which:

FIG. 6A-E are directed to experiments demonstrating that acrydite modified Oligopaints allow tethering of Oligopaint to ExM gel matrix. FIG. 6A is a schematic depicting Oligopaint with Acrydite modification. Acrydite (Yellow trapezoid) is incorporated onto the 5' end of each Oligopaint. Oligopaints are visualized with a fluorophore labeled secondary oligo binding to the Mainstreet (non-genomic sequence upstream of the complementary nucleic acid sequence. FIG. 6B-6E depict PGP1F cells stained with ~20,000 Oligopaints (green) targeting 2.1 Mb region on q arm of Chromosome 19 (9.2 probes/Kb) in ExM gel. Non-modified Oligopaints are shown in FIGS. 6B-6C. Acrydite modified Oligopaints are shown in FIGS. 6D-6E. Acrydite modified Oligopaints remain attached to Expansion gel after Oligopaint removal by treatment with 70% formamide at 73 degrees (FIG. 6E), while non-modified Oligopaints do not (FIG. 6C). Scale bar=10 microns.

DETAILED DESCRIPTION

Figure 1:
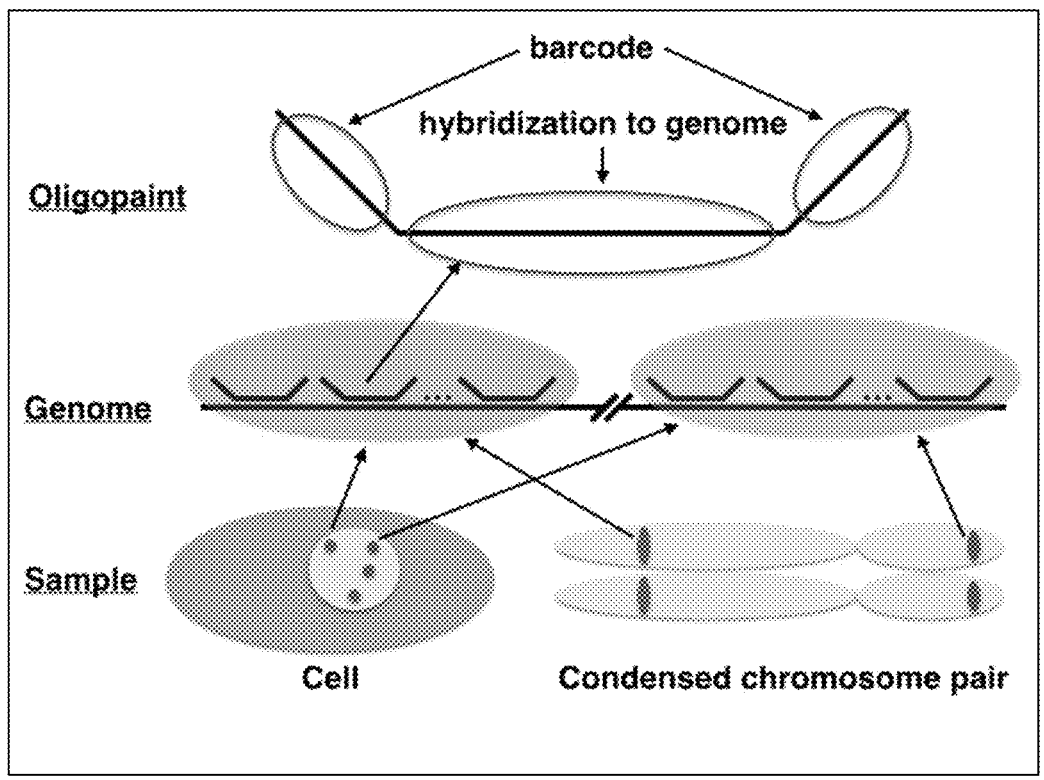
FIG. 1 is a schematic depicting hybridization of probes including barcodes to target genomic nucleic acids.

Terms and symbols of nucleic acid chemistry, biochemistry, genetics, and molecular biology used herein follow those of standard treatises and texts in the field, e.g., Kornberg and Baker, *DNA Replication*, Second Edition (W. H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

The disclosure provides use of a plurality or set of probes for hybridization with a given target genomic nucleic acid. The probes can cross a cell membrane and/or a nuclear membrane. The plurality or set of probes have a unique associated barcode to identify the probes within the plurality or set. The disclosure provides use of a plurality of sets of probes, such that a corresponding plurality of target genomic nucleic acids may be detected and identified, such as in a multiplexed manner. As the associated barcode is unique to the target genomic nucleic acid, sequencing the associated barcode using a fluorescence-based sequencing method allows one to detect and identify the target genomic nucleic acid. Since a plurality of sets of probes may be used, a plurality of target genomic nucleic acids, such as within a genome, may be detected and identified, such as in a multiplexed manner, where the plurality of sets probes are contacted with genomic DNA to hybridize to a plurality of corresponding target nucleic acids, the associated barcodes are sequenced using a fluorescence-based sequencing method, and the plurality of corresponding target nucleic acids are detected and identified. The disclosure provides the use of fluorescence-based sequencing methods such as sequencing by synthesis, sequencing by ligation, sequencing by hybridization, sequencing by cyclic reversible polymerization hybridization chain reaction (HCR) and the like. Since fluorescence-based sequencing methods are used to sequence an associated barcode corresponding to the plurality or set of probes hybridized to a given target genomic nucleic acid sequence, the fluorescent signal is effectively amplified by the number of probes hybridized to the given target nucleic acid sequence.

The disclosure provides that a barcode is associated with a plurality or set of oligonucleotide probes such that the barcode uniquely identifies the plurality or set of oligonucleotide probes and, therefore, the corresponding target genomic nucleic acid to which the plurality or set of oligonucleotide probes is hybridized. The disclosure provides that the barcode is associated with the plurality or set of oligonucleotide probes to the extent that each probe in the plurality or set includes the barcode. The disclosure provides that the barcode is associated with the plurality or set of oligonucleotide probes to the extent that each probe in the plurality or set includes a portion of an entire barcode, such that sequencing of the portions attached to the probes results in the sequencing of the entire barcode. The portions of the entire barcode need not be equal portions. The portions of the barcode may overlap and provide useful redundancy. Providing portions of an entire barcode on probes also advantageously shortens the length of the probe to more easily facilitate hybridization to a target genomic nucleic acid.

The disclosure provides methods where a plurality of oligonucleotide probes are hybridized to the genome, such that for every subset of the total pool of probes, which correspond to individual genomic loci to be labeled and detected, bears a unique identifying barcode sequence. Alternatively, the subset of probes targeting each single locus may bear a number of sequences that function as an ensemble barcode. For example, some probes may bear the first segment of the barcode, while others bear the second segment, and so on. The barcode sequence may be read out by sequencing by ligation, sequencing by synthesis or sequencing by hybridization, where the signal is effectively amplified by the number of probes at each locus bearing the barcode or particular segment (e.g. base) of the barcode. The barcode sequence may also be read out by sequencing by cyclic reversible polymerization hybridization chain reaction (HCR).

The disclosure provides a method of identifying a target genomic nucleic acid sequence including hybridizing a set of probes to the target genomic nucleic acid sequence, wherein the set of probes has a unique associated barcode sequence for identification of the target genomic nucleic acid sequence, wherein each probe of the set includes (1) a complementary sequence complementary to a first strand or a second strand of the target genomic nucleic acid sequence and (2) the associated barcode sequence or a portion of the associated barcode sequence, sequencing the associated barcode sequence from probes hybridized to the target genomic nucleic acid sequence using a fluorescence-based sequencing method, and identifying the target genomic nucleic acid sequence by the sequenced barcode sequence.

The disclosure provides that the fluorescence-based sequencing method is sequencing by synthesis and the probe further includes a priming sequence for annealing a sequencing primer, wherein the sequencing primer is extended by a DNA polymerase using reversible terminator fluorescently encoded dNTPs to generate a fluorescent signal corresponding to the barcode.

The disclosure provides that the fluorescence-based sequencing method is sequencing by ligation and the probe further includes a priming sequence for annealing a sequencing primer, wherein the sequencing primer is extended in either the 5' or 3' direction by a DNA ligase using fluorescently encoded oligonucleotides to generate a fluorescent signal corresponding to the barcode.

The disclosure provides that the fluorescence-based sequencing method is sequencing by hybridization and the probe further includes a first nucleic acid sequence complementary to a labeled oligonucleotide which hybridizes to the first nucleic acid sequence.

The disclosure provides that the fluorescence-based sequencing method is sequencing by cyclic reversible polymerization hybridization chain reaction.

The disclosure provides that a plurality of probes having a portion of the associated barcode sequence constitute a complete associated barcode sequence.

The disclosure provides that the complementary sequence has a nucleotide length of between 5 and 10,000 bases. The disclosure provides that the complementary sequence has a nucleotide length of between 15 and 1,000 bases. The disclosure provides that the complementary sequence has a nucleotide length of between 20 and 80 bases.

The disclosure provides that the probe includes one or more spacer sequences separating the complementary sequence from the associated barcode sequence or portion of the associate barcode sequence.

The disclosure provides that the probe includes one or more spacer sequences comprising a plurality of dT nucleotides separating the complementary sequence from the associated barcode sequence or portion of the associate barcode sequence.

The disclosure provides that the probe includes one or more spacer sequences separating functional sequences of the barcode including the complementary sequence, the associated barcode sequence or portion of the associate barcode sequence, and a priming sequence.

The disclosure provides that the probe includes one or more spacer sequences comprising a plurality of dT nucleotides separating functional sequences of the barcode including the complementary sequence, the associated barcode sequence or portion of the associate barcode sequence, and a priming sequence.

The disclosure provides that the target genomic nucleic acid has a length of between 10 bp and 1,000,000,000 bp. The disclosure provides that the target genomic nucleic acid has a length of between 20 bp and 1,000,000 bp. The disclosure provides that the target genomic nucleic acid has a length of between 100 bp and 1,000,000 bp. The disclosure provides that the target genomic nucleic acid has a length of between 100,000 bp and 1,000,000,000 bp. The disclosure provides that the target genomic nucleic acid is a whole genome.

The disclosure provides that the probe includes one or more additional barcode sequences for barcoding characteristics of the target genomic nucleic acid.

The disclosure provides that the probes are oligopaints.

The disclosure provides that the probes further include an attachment moiety for attachment to a matrix.

The disclosure provides for a method of multiplexing the identification of a plurality of target genomic nucleic acid sequences within genomic DNA including hybridizing the genomic DNA with a plurality of probe sets corresponding to the plurality of target genomic nucleic acid sequences, wherein each probe set has a unique associated barcode sequence for identification of the corresponding target genomic nucleic acid sequence, wherein each probe of each probe set includes (1) a complementary sequence complementary to a first strand of the corresponding target genomic nucleic acid sequence and (2) the associated barcode sequence or a portion of the associated barcode sequence, sequencing the associated barcode sequence from probes hybridized to the plurality of target genomic nucleic acid sequences using a fluorescence-based sequencing method, and identifying the target genomic nucleic acid sequence by the sequenced barcode sequence. The disclosure provides that the plurality of target genomic nucleic acid sequences within genomic DNA is between 5 and 100,000,000 target genomic nucleic acid sequences.

Probes

Nucleic acid sequences or oligonucleotide probes according to the present disclosure may have any desired length. The term "probe" refers to a single-stranded oligonucleotide sequence that will recognize and form a hydrogen-bonded duplex with a complementary sequence in a target nucleic acid sequence or its cDNA derivative. The probe includes a target hybridizing nucleic acid sequence. A probe provided by the disclosure includes a complementary sequence complementary to a strand of the target genomic nucleic acid sequence and the associated barcode sequence or a portion of the associated barcode sequence. Accordingly, the term "probe" may also be understood as including the barcode or any sequence feature needed for fluorescence-based sequencing of the barcode. Oligonucleotide or polynucleotide probes may be designed, if desired, with the aid of a computer program such as, for example, DNAWorks, or Gene2Oligo.

The complementary sequence may have a nucleotide length between about 15 and about 1000 bases. The complementary sequence may have a nucleotide length between about 15 and about 500 bases. The complementary sequence may have a nucleotide length between about 15 and about 400 bases. The complementary sequence may have a nucleotide length between about 15 and about 300 bases. The complementary sequence may have a nucleotide length between about 15 and about 200 bases. The complementary sequence may have a nucleotide length between about 15 and about 100 bases. The complementary sequence may have a nucleotide length between about 15 and about 90 bases. The complementary sequence may have a nucleotide length between about 15 and about 80 bases. The complementary sequence may have a nucleotide length between about 15 and about 70 bases. The complementary sequence may have a nucleotide length between about 15 and about 60 bases. The complementary sequence may have a nucleotide length between about 15 and about 50 bases. The complementary sequence may have a nucleotide length between about 15 and about 40 bases. The complementary sequence may have a nucleotide length between about 15 and about 30 bases. The complementary sequence may have a nucleotide length between about 20 and about 1000 bases. The complementary sequence may have a nucleotide length between about 20 and about 500 bases. The complementary sequence may have a nucleotide length between about 20 and about 100 bases. The complementary sequence may have a nucleotide length between about 20 and about 80 bases. The complementary sequence may have a nucleotide length between about 20 and about 40 bases. The complementary sequence may have a nucleotide length between about 20 and about 100 bases. The complementary sequence may have a nucleotide length between about 20 and about 60 bases. The complementary sequence may have a nucleotide length of about 22, 32, 40, 50 or 60 bases.

The disclosure provides for the optimization of the length of the complementary region based on one or more of the following: On-target vs. off-target thermodynamic specificity, [e.g. such that the thermodynamic penalty of a probe hybridizing off-target vs. on-target, which is related to the difference in free energy between the two hybridization states (off vs on target), is great enough that under particular hybridization reaction conditions (e.g. salt, formamide, temperature, competing probes, etc., which all effect the equilibrium constant of the hybridization reaction (A+B<>AB), the hybridization reaction will cause on-target hybridizations to be maximized while off-target hybridizations are minimized]; and hybridization reaction kinetics [e.g. that the reaction will be driven to a sufficient state of completion (1%, 10%, 20%, 50%, 100% of probes hybridized to the target) within a certain amount of reaction time], such that the genomic locus can be identified.

The disclosure provides probes which may be oligonucleotide or polynucleotide probes. Such oligonucleotide or polynucleotide probes may be referred to as Oligopaint probes or Oligopaints or chromosome paints as is known in the art. See US-2010-0304994 hereby incorporated by reference in its entirety. Oligopaint probes or Oligopaints or chromosome paints are detectable markers that label chromosomes along their entire length, permitting physicians and researchers to identify chromosomes and decipher chromosome rearrangements. The present disclosure provides the use of barcode sequences that, when sequenced, serve as detectable markers for the target genomic nucleic acid.

Probes, such as Oligopaints, have a high resolution useful in detecting and identifying target genomic nucleic acids. As used herein, the term "resolution" refers to the ability to distinguish (e.g., label) between two points on a polynucleotide sequence (e.g., two points along the length of a chromosome). As used herein, the term "high resolution" refers to the ability to detect two or more nucleic acid sequences having a distance of less than $6 \times 10^6$ base pairs apart (e.g., on a chromosome). In certain aspects, two or more high resolution Oligopaints have a resolution of about 500 kilobases apart or fewer, 400 kilobases apart or fewer, 300 kilobases apart or fewer, 200 kilobases apart or fewer, 100 kilobases apart or fewer, 90 kilobases apart or fewer, 80 kilobases apart or fewer, 70 kilobases apart or fewer, 60 kilobases apart or fewer, 50 kilobases apart or fewer, 40 kilobases apart or fewer, 30 kilobases apart or fewer, 20 kilobases apart or fewer, 19 kilobases apart or fewer, 18 kilobases apart or fewer, 17 kilobases apart or fewer, 16 kilobases apart or fewer, 15 kilobases apart or fewer, 14 kilobases apart or fewer, 13 kilobases apart or fewer, 12 kilobases apart or fewer, 11 kilobases apart or fewer, 10 kilobases apart or fewer, 9 kilobases apart or fewer, 8 kilobases apart or fewer, 7 kilobases apart or fewer, 6 kilobases apart or fewer, 5 kilobases apart or fewer, 4 kilobases apart or fewer, 3 kilobases apart or fewer, 2 kilobases apart or fewer or 1 kilobase apart or fewer. In certain aspects, two or more high resolution Oligopaints have a resolution of about 1900 bases apart or fewer, 1800 bases apart or fewer, 1700 bases apart or fewer, 1600 bases apart or fewer, 1500 bases apart or fewer, 1400 bases apart or fewer, 1300 bases apart or fewer, 1200 bases apart or fewer, 1100 bases apart or fewer, 1000 bases apart or fewer, 900 bases apart or fewer, 800 bases apart or fewer, 700 bases apart or fewer, 600 bases apart or fewer, 500 bases apart or fewer, 400 bases apart or fewer, 300 bases apart or fewer, 200 bases apart or fewer, 100 bases apart or fewer, 95 bases apart or fewer, 90 bases apart or fewer, 85 bases apart or fewer, 80 bases apart or fewer, 75 bases apart or fewer, 70 bases apart or fewer, 65 bases apart or fewer, 60 bases apart or fewer, 55 bases apart or fewer, 50 bases apart or fewer, 45 bases apart or fewer, 40 bases apart or fewer, 35 bases apart or fewer, 30 bases apart or fewer, 25 bases apart or fewer, 20 bases apart or fewer, 15 bases apart or fewer, 10 bases apart or fewer or down to the individual base pair. In certain aspects, two or more high resolution Oligopaints have a resolution of between about 10 bases and about 2000 bases, between about 10 bases and about 1000 bases, between about 10 bases and about 500 bases, between about 15 bases and about 250 bases, between about 15 bases and about 100 bases, between about 20 bases and about 50 bases, or between about 20 bases and about 30 bases.

As used herein, the term "sensitivity," with respect to probes, refers to the number of target nucleotide bases (e.g., target genomic nucleotide bases) that are complementary to a particular probe, i.e., the number of target nucleotide bases to which a particular probe can hybridize (i.e., the smallest band size that can be detected). In certain aspects, high resolution probes have a resolution of about 1 kilobase, about 1900 bases, about 1800 bases, about 1700 bases, about 1600 bases apart, about 1500 bases, about 1400 bases, about 1300 bases, about 1200 bases, about 1100 bases, about 1000 bases, about 900 bases, about 800 bases, about 700 bases, about 600 bases, about 500 bases, about 400 bases, about 300 bases, about 200 bases, about 100 bases, about 95 bases, about 90 bases, about 85 bases, about 80 bases, about 75 bases, about 70 bases, about 65 bases, about 60 bases, about 55 bases, about 50 bases, about 45 bases, about 40 bases, about 35 bases, about 30 bases, about 25 bases, about 20 bases, about 15 bases, about 10 bases, or about 5 bases. In certain aspects, the number of target nucleotide bases that are complementary to a probe are consecutive (e.g., consecutive genomic nucleotide bases).

The disclosure provides that probes are complementary to genomic nucleic sequences that are present in low or single copy numbers (e.g., genomic nucleic sequences that are not repetitive elements). As used herein, the term "repetitive element" refers to a DNA sequence that is present in many identical or similar copies in the genome. Repetitive elements are not intended to refer to a DNA sequence that is present on each copy of the same chromosome (e.g., a DNA sequence that is present only once, but is found on both copies of chromosome 11, would not be considered a repetitive element, and would be considered a sequence that is present in the genome as one copy). The genome consists of three broad sequence components: Single copy or at least very low copy number DNA (approximately 60% of the human genome); moderately repetitive elements (approximately 30% of the human genome); and highly repetitive elements (approximately 10% of the human genome). For a review, see Human Molecular Genetics, Chapter 7 (1999), John Wiley & Sons, Inc.

The disclosure provides the use of small probes, such as Oligopaints. As used herein, the term "small probe" refers to a probe of between about 5 bases and about 100 bases long, or a probe of about 5 bases, about 10 bases, about 15 bases, about 20 bases, about 25 bases, about 30 bases, about 35 bases, about 40 bases, about 45 bases, about 50 bases, about 55 bases, about 60 bases, about 65 bases, about 70 bases, about 75 bases, about 80 bases, about 85 bases, about 90 bases, about 95 bases, or about 100 bases. Small probes can access targets that are not accessible to longer oligonucleotide probes. For example, in certain aspects small probes can pass into a cell, can pass into a nucleus, and/or can hybridize with targets that are partially bound by one or more proteins, etc. Small probes are also useful for reducing background, as they can be more easily washed away than larger hybridized oligonucleotide sequences.

The present disclosure provides for the use of a plurality of probes with a unique barcode sequence to hybridize to, detect and identify a target nucleic acid sequence. The plurality of probes may be a set or library of probes with a unique associated barcode which uniquely identifies the library or set of probes, and therefore, the target genomic sequence to which they are hybridized. The library may contain multiple probes with sequence complementarity to a single genomic locus, where the genomic locus has sequence variation including substitutions, mutations, deletions, or insertions of bases, such that under certain hybridization conditions the probability of all probes binding to a locus exhibiting sequence variation is not equal, and is biased in favor of binding one probe containing the corresponding and complementary sequence variation or is capable of encoding the sequence variation and where specificity may be gained by competition between a set of such probes. The associated barcode may be in the form of a portion of the entire barcode on one or more probes, such that the total barcode sequence may be determined by sequencing the portions of the barcode sequence. The portions may be overlapping or nonoverlapping.

The disclosure provides the use of one or more spacer sequences or regions that separate functional regions of the probe, where the functional regions are defined as those involved in nucleic acid hybridization, signal amplification, or sequencing. Spacer sequences are designed to specifically not interact with itself, e.g. by intramolecular hybridization to form hairpins or other DNA secondary structures, or the target genomic sequence or other sequences with which it may contact, such as intermolecular hybridization to other probes, RNA molecules, or other genomic loci, or to not promote intermolecular affinity to other biomolecular features such as proteins. Exemplary spacer sequences are poly-T sequences including $d(T)_4$, $d(T)_6$, and $d(T)_8$.

The disclosure provides the design and use of multiple probes that hybridize to a target genomic locus to create a combined signal which can be used to detect and identify the target genomic locus. As an example, a plurality or set or library of DNA oligonucleotide probes are designed such that a number of DNA oligonucleotide probes bearing a single barcode are used to hybridize to a genomic locus, such that when sequenced the set of probes generates a combined signal with enhanced photon yield and signal-to-noise ratio.

Barcodes and Other Sequences for Use with Probes

The present disclosure provides for the use of barcode sequences to differentially label sets of probes from one another. A barcode sequence is designed to be unique to the set of probes so the barcode can be used to detect and identify the target genomic sequence by sequencing the barcode or portions of the barcode from the probes hybridized to the target genomic sequence. The barcodes are designed such that they do not hybridize to the target nucleic acid sequence. Barcode sequences may be oligonucleotide sequences between 4 and 40 nucleotides. Barcode sequences may be oligonucleotide sequences between 8 and 25 nucleotides. Barcode sequences may be oligonucleotide sequences between 8 and 20 nucleotides.

The disclosure provides that the barcode may include any desired number of nucleotides sufficient to identify a corresponding desired number of target genomic nucleic acid sequences. A barcode is an information-theoretical construct that yields an ordered sequence of fluorescent signals when interrogated over time. The architecture of the barcode is dependent on the sequencing method used. For example, using cyclic HCR, the interrogation method is sequencing by hybridization (SBH), and a typical hybridization reaction is capable of distinguishing between regions of sequence ~20-25 bp in length per ordered signal. Therefore, as an example, a barcode composed of 20 ordered signals would require, 20×25 nucleotides of "barcode sequence" on the probe set, library or pool (e.g. distributed among the probes targeting a single locus). Other exemplary SBH interrogation methods (e.g. oligoPAINT) uses 8-bp motifs, so a barcode composed of 20 ordered signals would include at least 8×20 nucleotides. For sequencing by synthesis and ligation, detection of individual nucleotides can serve as the readout of ordered signals, so therefore a barcode composed of 20 ordered signals could be contained in 1×20 nucleotides. For sequencing by ligation, detection of 5-nt motifs can serve as the readout of ordered signals, so a barcode composed of 20 ordered signals could be contained in 5×20 nucleotides. In this way, barcode sequences are always composed of nucleotide sequences, but the relationship between the length of the "barcode" and the length of the sequence representing the barcode may be far from 1:1 (e.g. 1:25 in the case of SBH for cyclic HCR).

The probes are designed such that they include features that allow the barcodes be sequenced using fluorescence-based sequencing methods such as sequencing by synthesis, sequencing by ligation, sequencing by hybridization or sequencing by cyclic reversible polymerization hybridization chain reaction as is known in the art.

For example, for sequencing by synthesis, each barcoding region contains a priming region, where a sequencing primer may be annealed to form a partially double-stranded region of DNA, and an arbitrary number of bases serving as a specific barcode that is used to identify the genomic loci, such that extension of the sequencing primer by a DNA polymerase using reversible-terminator fluorescently encoded dNTPs will generate a fluorescent signal corresponding to the barcode, i.e. the probe may further include a priming sequence for annealing a sequencing primer, wherein the sequencing primer is extended by a DNA polymerase using reversible terminator fluorescently encoded dNTPs to generate a fluorescent signal corresponding to the barcode.

For example, for sequencing by ligation, each barcoding region contains a priming region, where a sequencing primer may be annealed to form a partially double-stranded region of DNA, and an arbitrary number of bases serving as a specific barcode that is used to identify the genomic loci, such that extension of the sequencing primer in either the 5' or 3' direction by a DNA ligase using fluorescently encoded oligonucleotides will generate a fluorescent signal corresponding to the barcode, i.e. the probe may further include a priming sequence for annealing a sequencing primer, wherein the sequencing primer is extended in either the 5' or 3' direction by a DNA ligase using fluorescently encoded oligonucleotides to generate a fluorescent signal corresponding to the barcode.

For example, for sequencing by hybridization, each barcoding region contains one or more regions of DNA sequence which may be probed using complementary fluorescently labeled oligonucleotides by nucleic acid hybridization, including where the nucleic acid hybridization is by DNA PAINT, e.g. where the fluorescently labeled detecting oligos are not stably hybridized to the genomically-targeted probe, but rather exist in equilibrium state such that super-resolution microscopy is achieved by temporal separation of molecules beyond the diffraction limit by stochastic blinking, photon accumulation, and Gaussian fitting to determine the localization of the detecting probe.

The disclosure provides for the use of standard Next Generation sequencing chemistries and deep three dimensional imaging for high throughput information readout for sequencing of the barcodes described herein. The Next Generation sequencing chemistries that utilize fluorescence imaging include ABI SoLiD (Life Technologies), in which a sequencing primer on a template is ligated to a library of fluorescently labeled nonamers with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The workflow is achieved using an automated fluidics and imaging device (i.e. SoLiD 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (HiSeq, Illumia). General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use in the present methods. Reversible termination methods use step-wise sequencing-by-synthesis biochemistry that coupled with reversible termination and removable fluorescence (Shendure et al. supra and U.S. Pat. Nos. 5,750,341 and 6,306,597, incorporated herein by reference.) FISSEQ is a method useful for barcode sequencing whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, incorporated herein by reference in its entirety for all purposes. According to certain aspects, the barcodes can be interrogated using methods known to those of skill in the art including fluorescently labeled oligonucleotide/DNA/RNA hybridization, primer extension with labeled ddNTP, sequencing by ligation (i.e. ABI SoLiD) and sequencing by synthesis (i.e. Illumina). Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets.

The disclosure provides that the probe include an entire barcode sequence. The disclosure provides that the probe include a portion of a barcode sequence, such as where the entire barcode encoding the identity of the genomic loci is distributed among the multiple probes targeting a single genomic loci, such that each probe contains only a subset of the information in the full barcode, but in a manner such that the barcode may still be read out programmatically. As an example half the probes targeting a genomic locus contain five values of the barcode, sequencing of which is initiated using a particular sequencing primer, while the other half of the probes targeting the same genomic locus contain another five values of the barcode, sequencing of which is initiated using a second sequencing primer, enabling a ten-value barcode to be determined. As an example, each probe bears one segment of a barcode, which are read out sequentially in a deterministic order by cyclic reversible hybridization chain reaction (HCR).

The disclosure provides for the probe or the barcode to include error detection and/or error correction features. Error detection and correction methods suitable for use in the present disclosure are described at woorld wide website en.wikipedia.org/wiki/Error_detection_and_correction. For example, the barcode is constructed such that additional information is encoded beyond that necessary for identification. Exemplary additional information includes one or more sequences to effectively increase the Hamming distance between the encoded strings (e.g. constructing barcode in a barcode space of $4^{50}$ where only $4^{20}$ barcodes are needed to identify each genomic locus). For example, if a barcode is composed of 20 ordered detections of 4 identities ($4^{\wedge}20$ combinations), which is used to identify $4^{\wedge}20$ items, when a single error occurs in detecting the barcode [either 1) a missed signal or 2) an incorrect signal at any point in the barcode], one would either 1) be unable to distinguish between 4 possible items it could be or 2) could be misidentify the item, because all $4^{\wedge}20$ barcodes correspond to items to be detected. If one uses 50 ordered detections of 4 identities ($4^{\wedge}50$) to identify the same $4^{\wedge}20$ items, if you have an error as above, it is unlikely that the erroneous barcode will correspond to any of the $4^{\wedge}20$ real barcodes. Therefore, which real barcode is closest to the erroneous detected barcode in hamming distance is identified, and it is most likely to actually be that barcode. In this way, the method includes both detecting an error and correcting an error.

A probe or barcode may be constructed to incorporate error detection and/or correction codes such as parity bits, checksums, Golay encoding, or any other method for detecting and/or correcting errors. The present disclosure contemplates use of redundancy for error detection and correction. Barcode sequences are constructed such that they are two exact repeats of a smaller identifying label. When there is an error in detecting a certain signal, (missing signal—e.g. fluorescence is not identified) but is detected later in the redundant part of the barcode, at that time the signal is detected. The barcode can be accurately identified using a redundancy in the barcode sequence. The present disclosure contemplates use of Golay encoding for error detection and correction. For a binary ID/label of length 12 (12 ordered detections of 2 identities), on the actual probes, a longer barcode is used composed of 24 ordered detections of 2 identities ($2^{\wedge}24$) that is the binary Golay representation of the length-12 label, which contains additional ordered detections composed according to the Golay algorithm G24 (see world wide website en.wikipedia.org/wiki/Binary_Golay_code). When detecting the barcode, 24 ordered detections of 2 identities are read out, (Golay24 represents a binary string of length 12 using 24 bits), and then any 3 individual incorrect detection events can be corrected, or an error is detected from up to any 7 individual incorrect detection events, of the barcode composed of 24 detection events. An additional sequence or sequences may be included in the probe or barcode as needed to address other sources of error including if information is lost (e.g. hybridization is less than 100% complete, causing some subset of the probes to be missing at the genomic locus) or erroneous (e.g. a hybridization event is non-specific, generating a potential false-positive). For example, the entire barcode is divided among probes, such as when a 12-bit label is constructed into a 24 bit Golay24 barcode (barcode consisting of 24 ordered detections of 2 identities), and the 24-bit barcode is distributed among 24 probes targeting a locus such that each probe bears 1 part of the barcode. When hybridization is only 90% efficient, such that on average only 21 of the 24 probes make it to the target locus, using Golay encoding, up to 3 incorrect bits in a 12 bit label can be corrected using G24 encoding. Accordingly, missing 3 random bits of this 24 bit barcode does not prevent identification by the barcode.

Errors can be detected and/or corrected by using additional information that results from sequencing. For example, the encoded information in the barcode plus additional information for error correction/detection may be divided among multiple probes such that a single probe in the absence of the other probes may be identified as an error, or so that the information may still be reconstructed even with some probes missing. Additional cross-probe information may also be encoded, e.g. signal from two probes could be known to be free of error if each probe encodes information about the other probe.

The disclosure provides for a number of DNA oligonucleotide probes in a set to include one or more barcode regions used for identification of the genomic locus. The disclosure provides for a subset of probes in the set to contain additional barcoded information used to convey sequence variation, e.g. a probe containing complementary sequence to a genomic variation contains extra bases of the barcode or additional barcoding regions used to convey this additional sequence-variation information in addition to the information about the coordinates of the genomic locus bearing the particular locus barcode.

Target Genomic Sequence

The disclosure provides for the hybridization of probes to a target nucleic acid sequence, such as a target genomic nucleic acid sequence, where the probes have a unique associated barcode indicating the target genomic sequence. The target genomic nucleic acid sequence may be a genomic locus. The size of the genomic locus identified by a unique associated barcode may be between 100 bp and the whole genome. Exemplary lengths include that of a single histone (about 100-200 bp), a single gene (about 1-3 kb), a 1-2 Mb region of the genome, an arm of a chromosome (100 to 600 Mb) a single chromosome (100-1000 Mb), a whole genome (on the order of 1-2 Gb) (such as for distinguishing between whole bacterial genomes).

The disclosure provides that the target nucleic acid sequence may be a genomic nucleic acid sequence or region of a genomic nucleic acid, such as a chromosome or a sub-chromosomal region. The probes described herein can be used to detect and identify chromosomes and sub-chromosomal regions of chromosomes during various phases of the cell cycle including, but not limited to, interphase, preprophase, prophase, prometaphase, metaphase, anaphase, telophase and cytokenesis.

As used herein, the term "chromosome" refers to the support for the genes carrying heredity in a living cell, including DNA, protein, RNA and other associated factors. The conventional international system for identifying and numbering the chromosomes of the human genome is used herein. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, Homo, Drosophila, Caenorhabiditis, Danio, Cyprinus, Equus, Canis, Ovis, Ocorynchus, Salmo, Bos, Sus, Gallus, Solanum, Triticum, Oryza, Zea, Hordeum, Musa, Avena, Populus, Brassica, Saccharum and the like.

As used herein, the term "chromosome banding" refers to differential staining of chromosomes resulting in a pattern of transverse bands of distinguishable (e.g., differently or alternately colored) regions, that is characteristic for the individual chromosome or chromosome region (i.e., the "banding pattern"). Conventional banding techniques include G-banding (Giemsa stain), Q-banding (Quinacrine mustard stain), R-banding (reverse-Giemsa), and C-banding (centromere banding). The disclosure provides for the use of barcodes to achieve chromosome banding.

As used herein, the term "karyotype" refers to the chromosome characteristics of an individual cell, cell line or genome of a given species, as defined by both the number and morphology of the chromosomes. Karyotype can refer to a variety of chromosomal rearrangements including, but not limited to, translocations, insertional translocations, inversions, deletions, duplications, transpositions, anueploidies, complex rearrangements, telomere loss and the like. Typically, the karyotype is presented as a systematized array of prophase or metaphase (or otherwise condensed) chromosomes from a photomicrograph or computer-generated image. Interphase chromosomes may also be examined. The disclosure provides for the use of barcodes to achieve karotyping.

As used herein, the terms "chromosomal aberration" or "chromosome abnormality" refer to a deviation between the structure of the subject chromosome or karyotype and a normal (i.e., non-aberrant) homologous chromosome or karyotype. The deviation may be of a single base pair or of many base pairs. The terms "normal" or "non-aberrant," when referring to chromosomes or karyotypes, refer to the karyotype or banding pattern found in healthy individuals of a particular species and gender. Chromosome abnormalities can be numerical or structural in nature, and include, but are not limited to, aneuploidy, polyploidy, inversion, translocation, deletion, duplication and the like. Chromosome abnormalities may be correlated with the presence of a pathological condition or with a predisposition to developing a pathological condition. Chromosome aberrations and/or abnormalities can also refer to changes that are not associated with a disease, disorder and/or a phenotypic change. Such aberrations and/or abnormalities can be rare or present at a low frequency (e.g., a few percent of the population (e.g., polymorphic)). The disclosure provides for the use of barcodes to identify "chromosomal aberration" or "chromosome abnormality".

The disclosure provides that the target genomic nucleic acid sequence, such as DNA, can be inside the cell or on a substrate, such as glass, for example as by a "metaphase spread" technique where chromosomes are arrayed on a slide, which is common for karyotyping. The DNA could be in a natural or artificial conformation, e.g. stretched within a flow cell.

Making Probes

Probes described herein, whether a "chromosome paint" or an "Oligopaint" refers to polynucleotides have sequences complementary to an oligonucleotide sequence, e.g., a portion of a DNA sequence e.g., a particular chromosome or sub-chromosomal region of a particular chromosome. The term "probe" may also be understood as including the barcode or any sequence feature needed for fluorescence-based sequencing of the barcode.

In general, a plurality or set or library of nucleic acid probes, such as DNA oligonucleotides, may be synthesized using a DNA microarray, or a DNA chip. The oligonucleotides may contain one or more sequences used for the purpose of amplification by polymerase chain reaction (PCR), in vitro transcription (IVT), and other biochemical processing steps such as adding additional sequence by ligation or polymerization, single-stranding, and processing by restriction enzymes, in order to generate a final library of oligonucleotides. Such methods are known to those of skill in the art and are described in U.S. Pat. No. 9,476,089, US 2012-0295801 and US 2010-0304994 each of which are hereby incorporated by reference in its entirety.

Probes may be generated from synthetic probes and arrays that are, optionally, computationally patterned (rather than using natural DNA sequences and/or chromosomes as a template). Probes may be made by any suitable method including array based methods as described in US 2010-0304994. Such a method includes the steps of providing at least one solid support having a plurality of synthetic, single stranded oligonucleotide sequences attached thereto which may nor may not include a barcode sequence or portion of a barcode sequence, wherein a portion of each of the plurality of synthetic, single stranded oligonucleotide sequences is complementary to a portion of a specific chromosome sequence, synthesizing a plurality of complementary strands, each of which is complementary to a synthetic, single stranded oligonucleotide sequence attached to the at least one solid support, removing the plurality of complementary strands from the at least one solid support, amplifying the plurality of complementary strands, and optionally barcoding the plurality of complementary strands if needed to produce a set of barcoded oligonucleotide paints. Probes, such as Oligopaints or oligonucleotide paints, have a resolution of about two kilobases or fewer. In certain aspects, each probe has a resolution of about one kilobase or fewer or 100 bases or fewer. In certain aspects, the set of probes has a resolution of between about 20 bases and about 30 bases.

The disclosure provides that synthesis of oligonucleotide probes (e.g., Oligopaints) and/or amplification of oligonucleotide probes (e.g., Oligopaints) can be performed using a support. As used herein, the term "oligonucleotide" is intended to include, but is not limited to, a single-stranded DNA or RNA molecule, typically prepared by synthetic means. Nucleotides of the present invention will typically be the naturally-occurring nucleotides such as nucleotides derived from adenosine, guanosine, uridine, cytidine and thymidine. In certain aspects, multiple supports (tens, hundreds, thousands or more) may be utilized (e.g., synthesized, amplified, hybridized or the like) in parallel. Suitable supports include, but are not limited to, slides (e.g., microscope slides), beads, chips, particles, strands, gels, sheets, tubing (e.g., microfuge tubes, test tubes, cuvettes), spheres, containers, capillaries, microfibers, pads, slices, films, plates (e.g., multi-well plates), microfluidic supports (e.g., microarray chips, flow channel plates, biochips and the like) and the like. In various embodiments, the solid supports may be biological, nonbiological, organic, inorganic or combinations thereof. When using supports that are substantially planar, the support may be physically separated into regions, for example, with trenches, grooves, wells, or chemical barriers (e.g., lacking a lipid-binding coating). In exemplary embodiments, supports can be made of a variety of materials including, but not limited to glass, quartz, ceramic, plastic, polystyrene, methylstyrene, acrylic polymers, titanium, latex, sepharose, cellulose, nylon and the like and any combination thereof. Such supports and their uses are well known in the art.

Oligonucleotide sequences useful as probes may be prepared by any suitable method, e.g., the phosphoramidite method described by Beaucage and Carruthers ((1981) *Tetrahedron Lett.* 22: 1859) or the triester method according to Matteucci et al. (1981) *J. Am. Chem. Soc.* 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574, 146, 5,554,744, 5,428,148, 5,264,566, 5,141,813, 5,959,463, 4,861,571 and 4,659,774, incorporated herein by reference in its entirety for all purposes). Pre-synthesized oligonucleotides and chips containing oligonucleotides may also be obtained commercially from a variety of vendors.

In an exemplary embodiment, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single stranded DNA molecule of desired sequence. An exemplary type of instrument is the type shown in FIG. 5 of U.S. Pat. No. 6,375,903, based on the use of reflective optics. It is a desirable that this type of maskless array synthesizer is under software control. Since the entire process of microarray synthesis can be accomplished in only a few hours, and since suitable software permits the desired DNA sequences to be altered at will, this class of device makes it possible to fabricate microarrays including DNA segments of different sequence every day or even multiple times per day on one instrument. The differences in DNA sequence of the DNA segments in the microarray can also be slight or dramatic, it makes no difference to the process. The MAS instrument may be used in the form it would normally be used to make microarrays for hybridization experiments, but it may also be adapted to have features specifically adapted for the compositions, methods, and systems described herein. For example, it may be desirable to substitute a coherent light source, i.e., a laser, for the light source shown in FIG. 5 of the above-mentioned U.S. Pat. No. 6,375,903. If a laser is used as the light source, a beam expanded and scatter plate may be used after the laser to transform the narrow light beam from the laser into a broader light source to illuminate the micromirror arrays used in the maskless array synthesizer. It is also envisioned that changes may be made to the flow cell in which the microarray is synthesized. In particular, it is envisioned that the flow cell can be compartmentalized, with linear rows of array elements being in fluid communication with each other by a common fluid channel, but each channel being separated from adjacent channels associated with neighboring rows of array elements. During microarray synthesis, the channels all receive the same fluids at the same time. After the DNA segments are separated from the substrate, the channels serve to permit the DNA segments from the row of array elements to congregate with each other and begin to self-assemble by hybridization.

Other methods for synthesizing oligonucleotide probes (e.g., Oligopaints) include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotide probes is described, for example, in U.S. Pat. Nos. 5,143,854, 5,510, 270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be used as necessary. Other applicable methods include mechanical techniques such as those described in U.S. Pat. No. 5,384,261.

Additional methods applicable to synthesis and/or amplification of oligonucleotide probes (e.g., Oligopaints) on a single support are described, for example, in U.S. Pat. No. 5,384,261. For example reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites.

Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. One of skill in the art will recognize that there are alternative methods of forming channels or otherwise protecting a portion of the surface of the support. For example, a protective coating such as a hydrophilic or hydrophobic coating (depending upon the nature of the solvent) is utilized over portions of the support to be protected, sometimes in combination with materials that facilitate wetting by the reactant solution in other regions. In this manner, the flowing solutions are further prevented from passing outside of their designated flow paths.

Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Typical dispensers include a micropipette to deliver the monomer solution to the support and a robotic system to control the position of the micropipette with respect to the support, or an ink-jet printer. In other embodiments, the dispenser includes a series of tubes, a manifold, an array of pipettes, or the like so that various reagents can be delivered to the reaction regions simultaneously.

Pin-based methods for synthesis of oligonucleotide probes on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtitre dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In yet another embodiment, a plurality of oligonucleotide probes (e.g., Oligopaints) may be synthesized on multiple supports. One example is a bead based synthesis method which is described, for example, in U.S. Pat. Nos. 5,770,358, 5,639,603, and 5,541,061. For the synthesis of molecules such as oligonucleotides on beads, a large plurality of beads are suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In certain embodiments, a plurality of oligonucleotide probes (e.g., Oligopaints) may be synthesized, amplified and/or used in conjunction with beads and/or bead-based arrays. As used herein, the term "bead" refers to a discrete particle that may be spherical (e.g., microspheres) or have an irregular shape. Beads may be as small as approximately 0.1 μm in diameter or as large approximately several millimeters in diameter. Beads typically range in size from approximately 0.1 μm to 200 μm in diameter. Beads may comprise a variety of materials including, but not limited to, paramagnetic materials, ceramic, plastic, glass, polystyrene, methylstyrene, acrylic polymers, titanium, latex, sepharose, cellulose, nylon and the like. In certain aspects, beads may have functional groups on their surface which can be used to oligonucleotides (e.g., Oligopaints) to the bead. Oligonucleotide sequences can be attached to a bead by hybridization (e.g., binding to a polymer), covalent attachment, magnetic attachment, affinity attachment and the like. For example, the bead can be coated with streptavidin and the nucleic acid sequence can include a biotin moiety. The biotin is capable of binding streptavidin on the bead, thus attaching the nucleic acid sequence to the bead. Beads coated with streptavidin, oligo-dT, and histidine tag binding substrate are commercially available (Dynal Biotech, Brown Deer, Wis.). Beads may also be functionalized using, for example, solid-phase chemistries known in the art, such as those for generating nucleic acid arrays, such as carboxyl, amino, and hydroxyl groups, or functionalized silicon compounds (see, for example, U.S. Pat. No. 5,919,523).

Various exemplary protecting groups useful for synthesis of oligonucleotide probes on a solid support are described in, for example, Atherton et al., 1989, Solid Phase Peptide Synthesis, IRL Press. In various embodiments, the methods described herein utilize solid supports for immobilization of nucleic acids. For example, oligonucleotides may be synthesized on one or more solid supports. Exemplary solid supports include, for example, slides, beads, chips, particles, strands, gels, sheets, tubing, spheres, containers, capillaries, pads, slices, films, or plates. In various embodiments, the solid supports may be biological, nonbiological, organic, inorganic, or combinations thereof. When using supports that are substantially planar, the support may be physically separated into regions, for example, with trenches, grooves, wells, or chemical barriers (e.g., hydrophobic coatings, etc.). Supports that are transparent to light are useful when the assay involves optical detection (see e.g., U.S. Pat. No. 5,545,531). The surface of the solid support will typically contain reactive groups, such as carboxyl, amino, and hydroxyl or may be coated with functionalized silicon compounds (see e.g., U.S. Pat. No. 5,919,523).

In one embodiment, the oligonucleotide probes synthesized on the solid support may be used as a template for the production of oligonucleotide probes, such as Oligopaints. For example, the support bound oligonucleotides may be contacted with primers that hybridize to the oligonucleotides under conditions that permit chain extension of the primers. The support bound duplexes may then be denatured, pooled and subjected to further rounds of amplification to produce probes, such as Oligopaints, in solution. In another embodiment, the support-bound oligonucleotide probes may be removed from the solid, pooled and amplified to produce probes, i.e. Oligopaints, in solution. The oligonucleotides may be removed from the solid support, for example, by exposure to conditions such as acid, base, oxidation, reduction, heat, light, metal ion catalysis, displacement or elimination chemistry, or by enzymatic cleavage.

In various embodiments, the methods disclosed herein comprise amplification of oligonucleotide sequences, i.e., probes, including Oligopaints. Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification. The disclosure provides for the amplification of probes by in vitro transcription from a promoter to generate an amplified ssRNA pool, followed by reverse transcription to generate a ssDNA library using materials and methods known to those of skill in the art.

In general, high resolution oligonucleotide paints may be made by computationally determining genomic spacing of a plurality of synthetic, oligonucleotide sequences, wherein each of the plurality is complementary to a portion of a specific chromosome sequence, synthesizing the plurality of synthetic oligonucleotide sequences, and labelling the plurality of synthetic oligonucleotide sequences with a barcode or portion of an entire barcode to produce a plurality of oligonucleotide paints, wherein the set of oligonucleotide paints has a resolution of about two kilobases or fewer, and wherein each of a plurality of the oligonucleotide paints is complementary to a target nucleic acid sequence (e.g., a genomic sequence), such as of 40 consecutive nucleotide bases or fewer. Certain exemplary embodiments are directed to the use of computer software to automate design and/or interpretation of genomic spacings, complementary sequences and barcode sequences for each specific set of oligonucleotides or Oligopaints. Such software may be used in conjunction with individuals performing interpretation by hand or in a semi-automated fashion or combined with an automated system. In at least some embodiments, the design and/or interpretation software is implemented in a program written in the JAVA programming language. The program may be compiled into an executable that may then be run from a command prompt in the WINDOWS XP operating system. Unless specifically set forth in the claims, the invention is not limited to implementation using a specific programming language, operating system environment or hardware platform.

Probes Including Attachment Moieties

The disclosure provides probes that include a moiety for attachment to a matrix material to immobilize the probe within or on the matrix material, such as a 3D matrix, for purposes of amplification or sequencing. An exemplary attachment moiety that can be attached to probes described herein is an acrydite moiety that is covalently incorporated into a polyacrylamide matrix, or a primary amine that is covalently incorporated into a proteinaceous BSPEG matrix. Exemplary methods of attaching nucleic acids to matrices for purposes of amplification and/or sequencing are known to those of skill in the art as provided in WO2014/163886.

The disclosure provides that the nucleic acid probes are modified to incorporate a functional moiety for attachment to the matrix. The functional moiety can be covalently cross-linked, copolymerize with or otherwise non-covalently bound to the matrix. The functional moiety can react with a cross-linker. The functional moiety can be part of a ligand-ligand binding pair. dNTP or dUTP can be modified with the functional group, so that the function moiety is introduced into the DNA during amplification. A suitable exemplary functional moiety includes an amine, acrydite, alkyne, biotin, azide, and thiol. In the case of crosslinking, the functional moiety is cross-linked to modified dNTP or dUTP or both. Suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix. Suitable exemplary spacer moieties include polyethylene glycol, carbon spacers, photo-cleavable spacers and other spacers known to those of skill in the art and the like. Matrix forming materials include polyacrylamide, cellulose, alginate, polyamide, cross-linked agarose, cross-linked dextran or cross-linked polyethylene glycol. The matrix forming materials can form a matrix by polymerization and/or cross-linking of the matrix forming materials using methods specific for the matrix forming materials and methods, reagents and conditions known to those of skill in the art.

Hybridization of Probes to a Target Nucleic Acid Sequence

Hybridization of the probes of the invention to target chromosomes sequences can be accomplished by standard in situ hybridization (ISH) techniques (see, e.g., Gall and Pardue (1981) *Meth. Enzymol.* 21:470; Henderson (1982) *Int. Review of Cytology* 76:1). Generally, ISH comprises the following major steps: (1) fixation of the biological structure to be analyzed (e.g., a chromosome spread), (2) pre-hybridization treatment of the biological structure to increase accessibility of target DNA (e.g., denaturation with heat or alkali), (3) optional pre-hybridization treatment to reduce nonspecific binding (e.g., by blocking the hybridization capacity of repetitive sequences), (4) hybridization of the mixture of nucleic acids to the nucleic acid in the biological structure or tissue; (5) post-hybridization washes to remove nucleic acid fragments not bound in the hybridization and (6) detection of the hybridized labelled oligonucleotides (e.g., hybridized Oligopaints). The reagents used in each of these steps and their conditions of use vary depending on the particular situation. For instance, step 3 will not always be necessary as the probes described herein can be designed to avoid repetitive sequences. Hybridization conditions are also described in U.S. Pat. No. 5,447,841. It will be appreciated that numerous variations of in situ hybridization protocols and conditions are known and may be used in conjunction with the present invention by practitioners following the guidance provided herein.

As used herein, the term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." Oligonucleotide probes according to the present disclosure need not form a perfectly matched duplex with the single stranded nucleic acid, though a perfect matched duplex is exemplary. According to one aspect, oligonucleotide probes as described herein form a stable hybrid with that of the target sequence under stringent to moderately stringent hybridization and wash conditions. If it is expected that the probes will be essentially completely complementary (i.e., about 99% or greater) to the target sequence, stringent conditions will be used. If some mismatching is expected, with the result that the probe will not be completely complementary, the stringency of hybridization may be lessened. "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* $1^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA. It is to be understood that any desired stringency and/or conditions may be employed as desired.

Detection method(s) used will depend on the particular fluorescence-based sequencing methods used to sequence the barcodes of the Oligopaints. In certain exemplary embodiments, chromosomes and/or chromosomal regions having one or more Oligopaints bound thereto and having fluorescent moieties associated therewith because of the fluorescence-based sequencing method may be detected using a microscope, a spectrophotometer, a tube luminometer or plate luminometer, x-ray film, a scintillator, a fluorescence activated cell sorting (FACS) apparatus, a microfluidics apparatus or the like. Detection may be accomplished using detection devices commonly use with FISSEQ methods known to those of skill in the art.

The in situ hybridization methods described herein can be performed on a variety of biological or clinical samples, in cells that are in any (or all) stage(s) of the cell cycle (e.g., mitosis, meiosis, interphase, G0, G1, S and/or G2). Examples include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. Samples are prepared for assays of the invention using conventional techniques, which typically depend on the source from which a sample or specimen is taken. These examples are not to be construed as limiting the sample types applicable to the methods and/or compositions described herein.

The following examples are set forth as being representative of the present invention. These examples are not to be construed as limiting the scope of the invention as these and other equivalent embodiments will be apparent in view of the present disclosure, figures, tables, and accompanying claims.

Nucleic Acid

The terms "nucleic acid," "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Oligonucleotides or polynucleotides useful in the methods described herein may comprise natural nucleic acid sequences and variants thereof, artificial nucleic acid sequences, or a combination of such sequences. Oligonucleotides or polynucleotides may be single stranded or double stranded.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Oligonucleotide sequences, such as single stranded oligonucleotide sequences, may be isolated from natural sources, synthesized or purchased from commercial sources. In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; Synthetic DNA Arrays In Genetic Engineering, Vol. 20:111, Plenum Press (1998); Duggan et al. (1999) *Nat. Genet.* S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

Polymerase recognition sites, cleavage sites and/or label or detectable moiety addition sites may be added to the single stranded oligonucleotides during synthesis using known materials and methods.

Solid Phase Supports or Substrates

In certain exemplary embodiments, one or more template nucleic acid sequences, i.e. oligonucleotide sequences, described herein are immobilized on a support or substrate made of materials known to those of skill in the art such glass or polymeric materials (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. When using a support that is substantially planar, the support may be physically separated into regions, for example, with trenches, grooves, wells, or chemical barriers (e.g., hydrophobic coatings, etc.).

In certain exemplary embodiments, a support is a microarray. As used herein, the term "microarray" refers in one embodiment to a type of assay that comprises a solid phase support having a substantially planar surface on which there is an array of spatially defined nonoverlapping regions or sites that each contain an immobilized nucleic acid such as a hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate create a substantially planar surface. Spatially defined sites may additionally be "addressable" in that its location and the identity of the immobilized probe at that location are known or determinable.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, oligonucleotides are immobilized via one or more of the cleavable linkers described herein. One or more or a plurality of cleavable moieties may also be located internally within the oligonucleotides, thereby providing sites to cleave a rolling circle amplification product into smaller nucleic acid sequences. The density of nonoverlapping regions containing nucleic acids in a microarray is typically greater than 100 per $cm^2$, and more typically, greater than 1000 per $cm^2$. Microarray technology relating to nucleic acid sequences is reviewed in the following exemplary references: Schena, Editor, Microarrays: A Practical Approach (IRL Press, Oxford, 2000); Southern, *Current Opin. Chem. Biol.,* 2: 404-410 (1998); Nature Genetics Supplement, 21:1-60 (1999); and Fodor et al, U.S. Pat. Nos. 5,424,186; 5,445,934; and 5,744,305. Oligonucleotides bound to a solid support useful in the present methods are commercially available and can be designed and made using methods known to those of skill in the art.

Methods of immobilizing oligonucleotides to a support are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861; nitrocellulose: Ranki et al. (1983) *Gene* 21:77; cellulose: Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169:104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

Example I

FIG. 1 depicts a DNA oligonucleotide probe, referred to here as an "oligopaint," is designed to contain a region for hybridization to the genome (complementary region or sequence), as well as two barcode-containing regions flanking the complementary region. It is to be understood that only a single barcode region on either side of the complementary region, i.e. 5' or 3' side, can be used. A plurality of probes is hybridized to the genome indicated in red and blue. Multiple probes complementary to a contiguous region of the genome indicated in red or blue bear a single unique associated barcode. It is to be understood that any number of contiguous regions of the genome can be targeted with probes having a unique associated barcode for a particular contiguous region. The barcodes are used for fluorescent identification of the genomic locus inside fixed cells or along the condensed chromatin of a metaphase spread.

Figure 2:
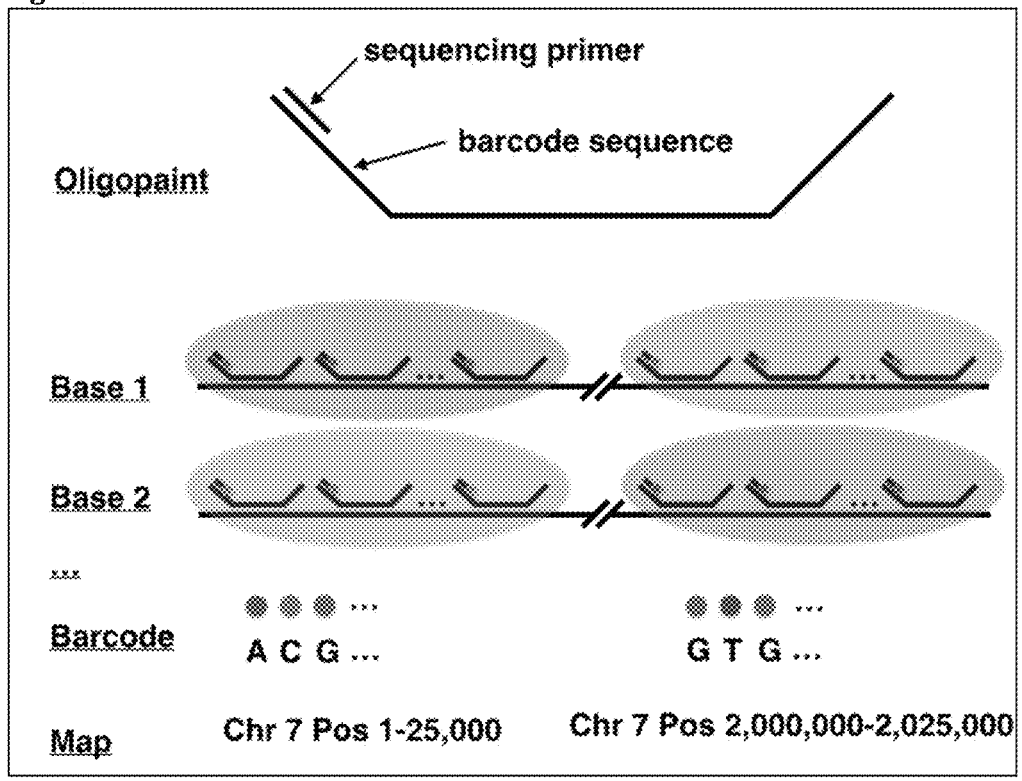
FIG. 2 is a schematic of a fluorescence based sequencing method used to sequence the barcodes of probes hybridized to target genomic nucleic acids.

FIG. 2 depicts that the DNA oligonucleotide probe, referred to here as an "oligopaint," is designed to incorporate a barcode-containing region compatible with sequencing by ligation, sequencing by synthesis, or sequencing by hybridization. Information contained in the barcode is read out fluorescently to generate a barcode, which can be computationally mapped to a genomic locus based on the design of the probe library. Here two genomic loci, each 25 kilobases in length, are given distinct barcodes and detected using a number of probes. Using a large number of probes to barcode a single genomic locus increases the photon yield and signal-to-noise ratio for fluorescent microscopic detection.

Figure 3:
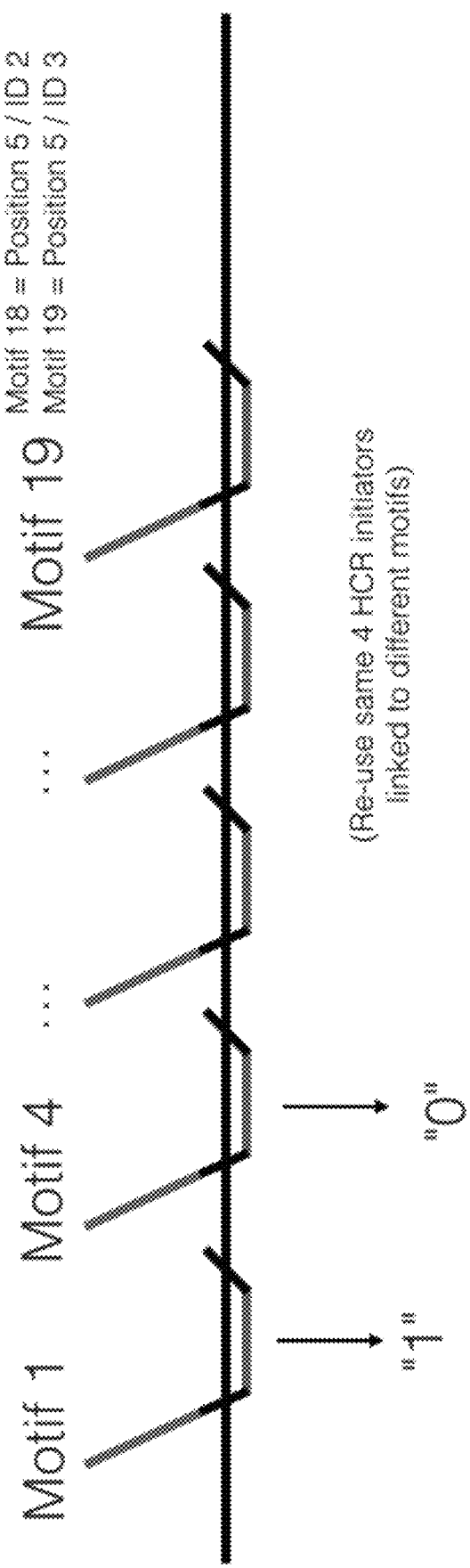
FIG. 3 is a schematic of the use of cyclic reversible polymerization hybridization chain reaction (HCR) for sequencing of barcodes.

FIG. 3 depicts that a genomic locus is targeted by a plurality of oligopaint probes, each bearing a subset of the identifying barcode for the genomic locus. For each oligopaint, regions bearing complementarity to the genomic locus, which drive targeted hybridization to the genomic locus, are in blue. Barcode encoding regions are in red, spacers are in black. To detect the first segment of the barcode, four linkers are hybridized to the sample, followed by HCR to generate an amplified fluorescent signal in one of four spectrally distinct colors. At this locus, the ID "1" is determined at the first segment of the barcode. The HCR is reversed and the linker is cleaved as in cyclic reversible HCR. A second round of linker hybridization and HCR occurs, identifying ID 0 as the second segment of the barcode. This process is repeated until a complete barcode is recovered.

Figure 4:
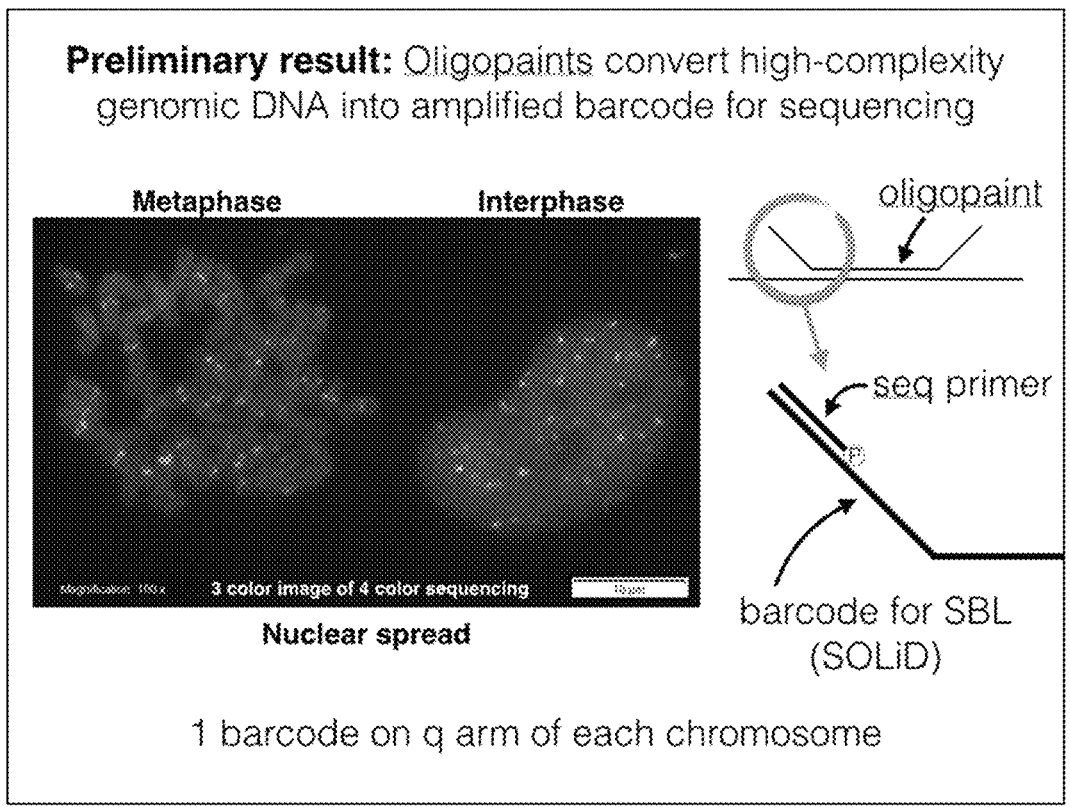
FIG. 4 depicts the results of an experiment directed to the sequencing of barcodes hybridized to target genomic nucleic acids.

FIG. 4 depicts a pool of oligopaints hybridized against a metaphase spread genome (left) and an intact nucleus (right). The oligopaint pool is designed such that a subset of the pool is targeted to a single site on the q arm of each chromosome, approximately 100 kb in size. (Hundreds of probes are targeted to each site). All oligopaints for each locus bear a distinct barcode designed to be detected by sequencing by ligation (SBL). A sequencing probe is hybridized to the oligopaints, and SBL is used to detect the first segment, in this case the first base, of a nucleic acid barcode sequence. Shown is a 3 color image of a 4 color sequencing reaction. After sequencing 5 bases with SBL, each barcode is identified, such that the target locus is labeled and detected in situ.

Example II

Oligopaints are Sequenced Using FISSEQ within an Expanded Matrix

PGP1F cells were plated onto glass microscope slides and were allowed to adhere overnight at 37° C. in a cell culture incubator. On the next day, cells on slides were transferred to coplin jars and washed 1× with 1×PBS, followed by fixation with 4% formaldehyde in PBS for 10 min at RT (room temperature). Another 1×PBS wash was performed and cells were permeabalized in 1×PBS+0.5% Triton X-100 for 10 min at RT. Two 1×PBS+0.1% Triton X-100 (1×PBT) washes for 5 minutes were performed at RT for 5 min each. Slides could then be stored in 1×PBT at 4° C. or be used for experiments. If proceeding to experiments, slides were treated in 0.1N HCl for 5 min at RT. Two washes in 2×SSCTween for 5 min at RT were performed. Next, prehybridization was done in 50% formamide in 2×SSCT solution for 5 min at RT. Another wash in same buffer was done at 60° C. for 20 min. Slides were slightly air-dried and 25 uL of probe solution including 100 pmols of Oligopaints in 50% formamide, 10% Polyacrylic Acid, 2×SSCT, and 20 mg RNAse1 were added to each slide, covered with a 22×22 mm cover slip and sealed with rubber cement. Probes were hybridized 0/N at 42° C. in a humid chamber. The next day, rubber cement and coverslips were carefully removed. Unbound probes were washed off with 2×SSCT at 60° C. for 20 min. 2×2×SSCT washes were performed at RT for 5 min each, followed by 0.2×SSC wash for 5 min at RT. 30 uL of ExM gel was cast over cells on slide using gelation chamber (parafilm wrapped glass microscope slide with 2 22×22 1.5 coverslips used as spacers) and allowed to polymerize at 37° C. for 1 hr. After polymerization, gelation chamber was carefully removed and gels on slide were digested 0/N in digestion buffer and 1:100 of NEB Proteinase K (20 mg/mL) at 37° C. Following digestion, glass slides were removed and gels were expanded in 1×PBS by shaking 2× for 7 min at RT. To ensure that gels remained expanded during subsequent steps, gels were re-embedded. Gels were tilted in 1.5 mL tube with 3% Acrylamide/BIS in 1×PBS with 0.05% APS and 0.05% TEMED for 20 min at RT. Gels were then removed and placed on microscope slide. A piece of 1.5 coverslip, broken to be big enough to cover the gel, was placed over the gel. Covered gels on microscope slide were placed in humid chamber that was filled with Argon gas to remove oxygen from chamber. Gelling proceeded at 37° C. for 1 hr. Re-embedded gels were washed 1× for 7 min in 100 mM MES at RT. Samples were passivated for 2 hrs at RT in 150 mM EDC, 150 mM NHS, 2M Ethanolamine hydrochloride, and 5M NaCl. Ethanolamine was then reacted for 40 min at RT by adding 2M Ethanolamine hydrochloride, 62.5 mM Sodium Borate Buffer (pH 8.5), and 5M NaCl to gels. Gels were then washed 3× in 1× SoLiD Instrument Buffer for 10 min at RT. Wash in 1×T4 Ligase Buffer for 7 min at RT was done to prepare for Oligopaint circularization. Oligopaints were then circularized by adding 2 uM Oligo Splint in 1×T4 Ligase Buffer and T4 DNA Ligase for 2 hrs at RT with gentle shaking. Samples were then washed 2× in 1× Instrument buffer for 7 min at RT, followed by washing in 1×NEB Buffer 1 for 7 min at RT. ssDNA and non-circularized Oligopaints were degraded by 1 uL NEB Exonuclease I in 1× Exonuclease I Buffer for 45 min at 37° C.

Figure 5:
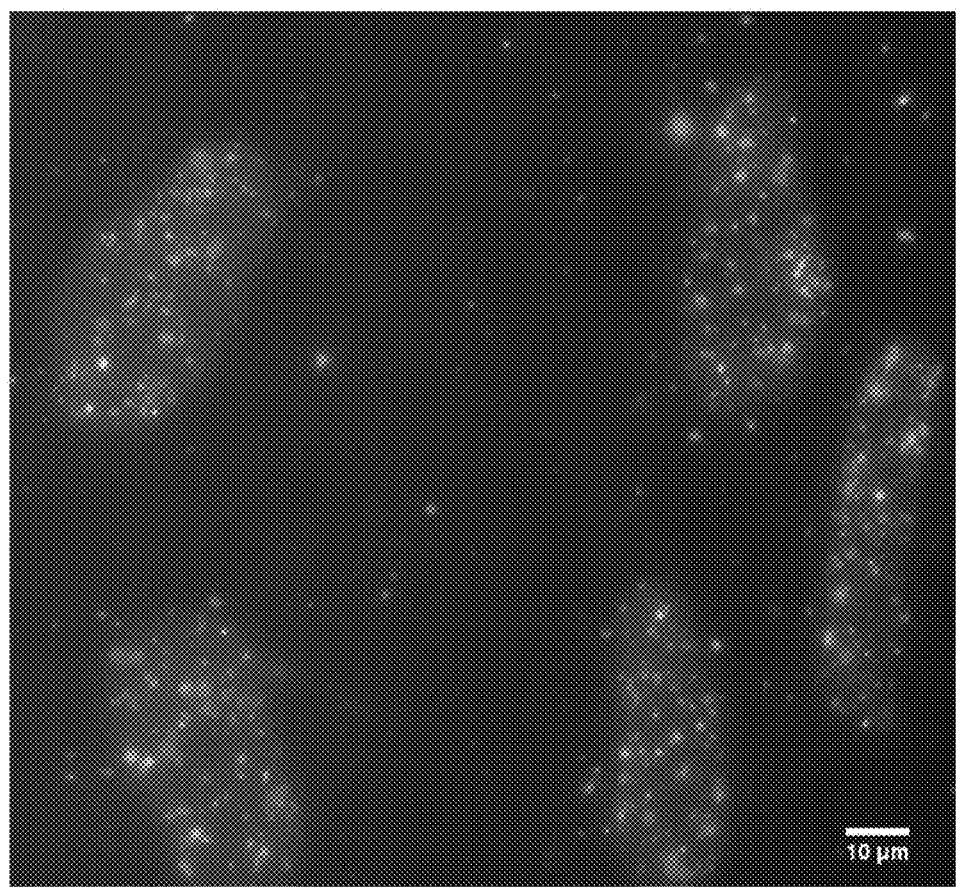
FIG. 5 is an image of cells with an expandable matrix having undergone in situ genome sequencing. IMR90 cells were stained with Oligopaints targeting 300 Kb-1 Mb unique regions on each chromosome with 3750 Oligopaints per region (~8 probes/Kb). Cells were then expanded ~4.5× in ExM gel. Oligopaint circularization, followed by Rolling Circle Amplifcation, and 1 round of sequencing by ligation was performed. Various colors represent 1 base of SoliD sequencing. Scale bar=10 microns.

3×1× instrument buffer washes for 7 min at RT, then 1×10 min wash in 30% formamide in 2×SSC at RT. Hybridization of 1 uM Rolling Circle Amplification (RCA) primer (same as Splint) was done in 30% formamide and 2×SSC for 1 hr at RT. After RCA primer hybridization, samples were washed 2×10 min in instrument buffer followed by 1×10 min in Phi29 Polymerase Buffer. RCA was performed by adding 1×Phi29 buffer, 250 uM dNTPs, 20 uM aminoallyl dUTP, and 2 Units of Phi29 DNA polymerase O/N at 30° C. RCA amplicons were crosslinked for 30 min at RT in 20 uL BS(PEG)9 in 980 uL 1×PBS. Quenching of BS(PEG)9 was done by incubating samples in 1M Tris (pH 8.0) for 45 min. Quenched samples were then washed 3×10 min in 1× instrument buffer at RT. To prepare for sequencing, 2.5 uM sequencing primer in 5×SSCT was hybridized for 1 hr at RT. 2×10 min washes in 1× instrument buffer was done, followed by washing in 1×T4 DNA ligase buffer for 10 min at RT. To sequence, 1×T4 ligation buffer, 5 uL of T4 DNA ligase, 1 uL of SoLiD sequencing nucleotide mix, with 84 uL of water was added to each sample for 2 hrs at RT. Samples were then washed with 1× instrument buffer for 1 hr at RT before imaging. FIG. 5 shows that Oligopaint circularization, followed by Rolling Circle Amplification, and 1 round of SoLiD sequencing by ligation is achieved in-situ, in fixed and expanded human cells.

Example III

Oligopaints with an Acrydite Attachment Moiety are Attached to a Matrix and Hybridized with a Secondary Oligo Bearing a Detectable Moiety Oligopaint library was first PCR amplified linearly to limit PCR errors. PCR product was column purified and resuspended in water. This linear product was PCR amplified again and T7 promoter sequences were added to each backstreet (non-genomic sequence downstream of the complementary sequence) via reverse primer. 1.3 ug of purified PCR products were in-vitro transcribed O/N at 37° C. This RNA served as the template for reverse transcription using forward primers containing 5' Acrydite modification to append Acrydite to Oligopaint. RNA was degraded by alkaline hydrolysis. Samples were then purified with Zymo 100 column purification kit, using Oligobinding Buffer instead of DNA binding buffer. Acrydite modified oligopaints were then used in standard FISH protocol. Following O/N hybridization of Acrydite modified Oligopaints, ExM (expandable matrix) gel was cast over samples using gelation chamber and allowed to polymerize at 37° C. for 1 hr. Gels were digested O/N in digestion buffer with 1:100 Proteinase K (NEB). Gels were washed 3×30 min in 2×SSCT. Gels were then cut and separated such that some samples could be probed with secondary oligo (Sample N) and some could be denatured prior to probing with secondary probe (Sample D) to assess tethering to ExM gel matrix. Sample N were kept in 2×SSCT at RT. Sample D were incubated in 70% formamide/2×SSC at 73° C. for 3 min 2× to confirm tethering of Acrydite modified Oligopaint to matrix. Sample D was then washed with 2×SSCT 2× for 10 min at RT. 3.3 uM secondary oligos were hybridized to Sample N and D for 1 hr at RT. Gels were washed in 30% formamide in 2×SSCT for 2× at RT for 30 min. 2 washes in 2×SSCT for 10 min were performed, followed by 1:500 DAPI in PBS staining for 20 min at RT. Samples were then imaged. FIG. 6A-6E are directed to the successful synthesis of Oligopaints with an Acrydite modification at the 5' end as the Oligopaints remain tethered and are able to be hybridized by a secondary oligo after treatment with high concentration of formamide with heating (FIG. 6E). This is in contrast to non-modified Oligopaints that are no longer present in the sample.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. Other embodiments will be evident to those of skill in the art. It should be understood that the foregoing description is provided for clarity only and is merely exemplary. All publications, patents and patent applications cited above are incorporated by reference herein in their entirety for all purposes to the same extent as if each individual publication or patent application were specifically indicated to be so incorporated by reference.

What is claimed is:

1. A method of identifying a target genomic nucleic acid sequence comprising:
   hybridizing a set of probes to the target genomic nucleic acid sequence, wherein the set of probes has a unique associated barcode sequence for identification of the target genomic nucleic acid sequence, wherein each probe of the set includes:
   (1) a complementary sequence complementary to a first strand or a second strand of the target genomic nucleic acid sequence,
   (2) the unique associated barcode sequence or a portion of the associated barcode sequence, and
   (3) one or more additional barcode sequences;
   sequencing the unique associated barcode sequence from probes hybridized to the target genomic nucleic acid sequence using a fluorescence-based sequencing method,
   identifying the target genomic nucleic acid sequence by the sequenced unique barcode sequence.

2. The method of claim 1, comprising detecting the one or more additional barcode sequences.

3. The method of claim 2, wherein detecting the one or more additional barcode sequences comprises hybridizing a detectably labeled nucleic acid molecule to the one or more additional barcode sequences.

4. The method of claim 1, wherein the probe comprises at least two different priming sequences for annealing at least two different sequencing primers.

5. The method of claim 4, wherein at least one priming sequence is positioned to initiate sequencing of the unique associated barcode sequence, and wherein at least one different priming sequence is positioned to initiate sequencing of the one or more additional barcode sequences.

6. The method of claim 1, wherein the probe comprises at least one priming sequence for annealing at least one amplification primer.

7. The method of claim 1, wherein sequencing the unique associated barcode sequence comprises amplifying the probe, or a portion of the probe comprising the unique associated barcode sequence.

8. The method of claim 1, wherein identifying the target genomic nucleic acid sequence comprises super-resolution microscopy.

9. The method of claim 1, wherein identifying the target genomic nucleic acid sequence comprises Gaussian fitting of the fluorescence signal from the barcode.

10. The method of claim 1, wherein after the hybridizing step, the method comprises contacting the target nucleic acid with an expandable matrix (ExM) gel.

11. A method of multiplexing the identification of a plurality of target genomic nucleic acid sequences within genomic DNA comprising:
hybridizing the genomic DNA with a plurality of probe sets corresponding to the plurality of target genomic nucleic acid sequences, wherein each probe set has a unique associated barcode sequence for identification of the corresponding target genomic nucleic acid sequence, wherein each probe of each probe set includes:
(1) a complementary sequence complementary to a first strand or a second strand of the target genomic nucleic acid sequence,
(2) the unique associated barcode sequence or a portion of the associated barcode sequence, and
(3) one or more additional barcode sequences;
sequencing the unique associated barcode sequence from probes hybridized to the plurality of target genomic nucleic acid sequence using a fluorescence-based sequencing method,
identifying the target genomic nucleic acid sequence by the sequenced unique barcode sequence.

12. The method of claim 11, comprising detecting the one or more additional barcode sequences.

13. The method of claim 12, wherein detecting the one or more additional barcode sequences comprises hybridizing a detectably labeled nucleic acid molecule to the one or more additional barcode sequences.

14. The method of claim 11, wherein each probe in each set of probes comprises at least two different priming sequences for annealing at least two different sequencing primers.

15. The method of claim 14, wherein at least one priming sequence is positioned to initiate sequencing of the unique associated barcode sequence, and wherein at least one different priming sequence is positioned to initiate sequencing of the one or more additional barcode sequences.

16. The method of claim 11, wherein each probe in each set of probes comprises at least one priming sequence for annealing at least one amplification primer.

17. The method of claim 11, wherein sequencing the unique associated barcode sequence comprises amplifying the probes, or a portion of the probes comprising the unique associated barcode sequence.

18. The method of claim 11, wherein identifying the target genomic nucleic acid sequence comprises super-resolution microscopy.

19. The method of claim 11, wherein identifying the target genomic nucleic acid sequence comprises Gaussian fitting of the fluorescence signal from the barcode.

20. The method of claim 11, wherein after the hybridizing step, the method comprises contacting the target nucleic acid with an expandable matrix (ExM) gel.

* * * * *